(12) United States Patent
Cushchieri et al.

(10) Patent No.: US 6,699,255 B1
(45) Date of Patent: Mar. 2, 2004

(54) DEVICE FOR ENDOSCOPIC DELIVERY OF SURGICAL MATERIAL

(75) Inventors: Alfred Cushchieri, Fife (GB); Graham Timothy Frank, Fife (GB)

(73) Assignee: University Court of the University of Dundee, Dundee (GB)

(*) Notice: Subject to any disclaimer, the term of this patent is extended or adjusted under 35 U.S.C. 154(b) by 0 days.

(21) Appl. No.: 09/530,444

(22) PCT Filed: Nov. 2, 1998

(86) PCT No.: PCT/GB98/03263
§ 371 (c)(1),
(2), (4) Date: Jul. 19, 2000

(87) PCT Pub. No.: WO99/22650
PCT Pub. Date: May 14, 1999

(30) Foreign Application Priority Data

Oct. 31, 1997 (GB) .............................................. 9722939

(51) Int. Cl.⁷ .............................................. A61B 17/10
(52) U.S. Cl. .................. 606/139; 606/142; 606/144
(58) Field of Search ................ 606/139, 142, 606/144, 148, 153, 146, 103, 213, 215–217, 219–221, 104, 75; 83/950; 24/27; 227/135, 136, 137, 138, 139, 180.1, 176.1, 179.1, 175.1; 140/123, 123.6, 139

(56) References Cited

U.S. PATENT DOCUMENTS

| | | | |
|---|---|---|---|
| 4,316,469 A | | 2/1982 | Kapitanov |
| 4,400,170 A | | 8/1983 | McNaughton et al. |
| 4,485,816 A | * | 12/1984 | Krumme ...................... 606/219 |
| 4,553,543 A | * | 11/1985 | Amarasinghe ............... 606/148 |
| 5,037,433 A | | 8/1991 | Wilk et al. |
| 5,188,636 A | | 2/1993 | Fedotov |
| 5,403,326 A | * | 4/1995 | Harrison et al. ............. 606/139 |
| 5,417,700 A | * | 5/1995 | Egan ........................... 606/144 |
| 5,545,171 A | * | 8/1996 | Sharkey et al. .............. 606/148 |
| 5,819,609 A | * | 10/1998 | Habermehl .................. 227/136 |
| 5,989,268 A | * | 11/1999 | Pugsley, Jr. et al. ......... 606/215 |
| 6,132,438 A | * | 10/2000 | Fleischman et al. ........ 606/139 |

FOREIGN PATENT DOCUMENTS

WO  WO9205828  4/1992

* cited by examiner

Primary Examiner—Julian W. Woo
(74) Attorney, Agent, or Firm—Howard & Howard

(57) ABSTRACT

A device for the delivery of a shape memory securing member into a confined space, the device having an exit for the securing member and means to move the securing member through the exit, the device further including a magazine having a plurality of channels each of which can store a securing member is described. Preferably, each securing member is restrained in the device in a first configuration, and upon passing through the exit adopts a second configuration. One form of the magazine is a barrel. The barrel may be rotatable around an axis, and the channels can be disposed parallel to said axis or may lie in a helical configuration. This arrangement can be likened to a "revolver barrel" on a firearm. One advantage of the present invention in surgery is that it can store several sutures or ligature multiple placements without the need to withdraw the instrument from the patient.

39 Claims, 5 Drawing Sheets

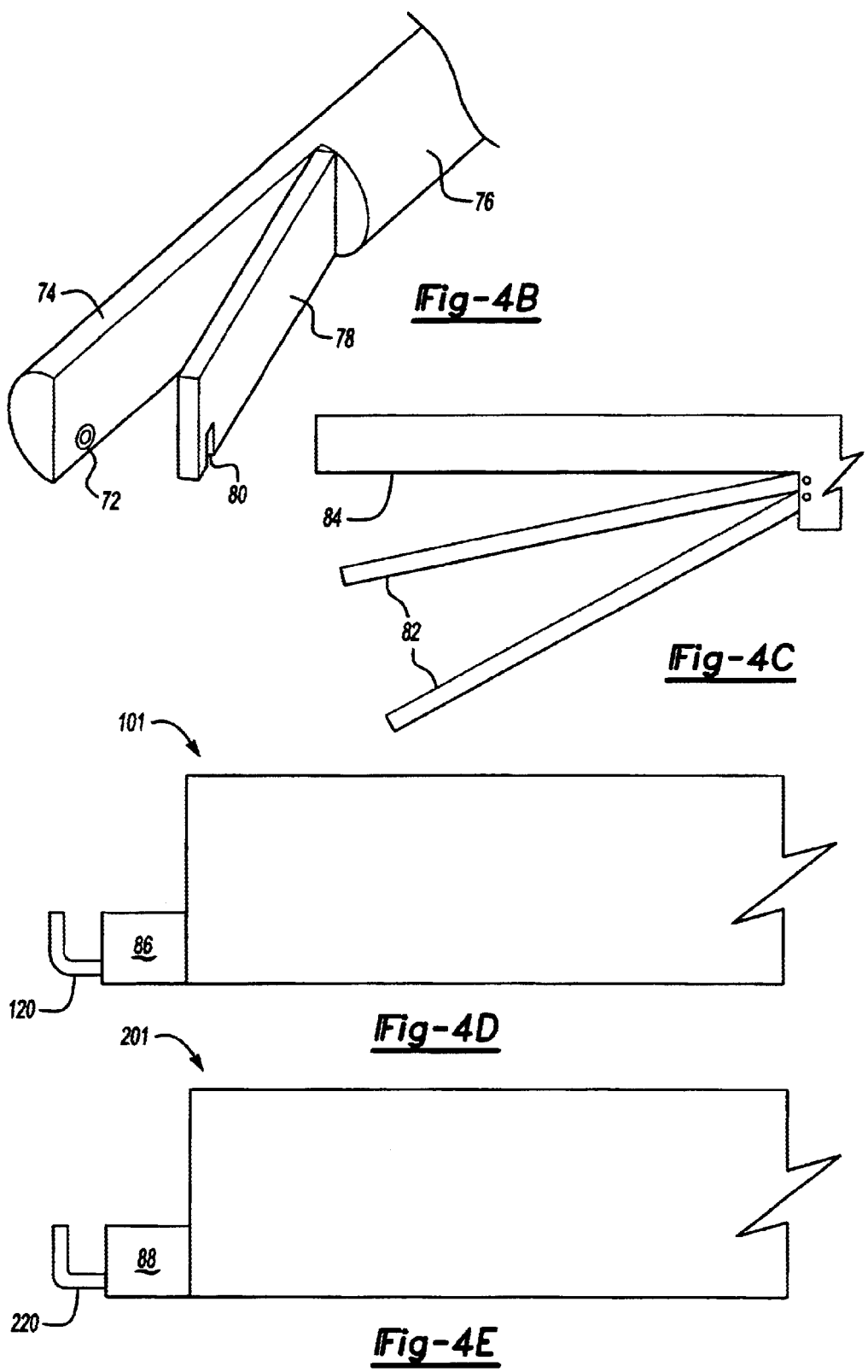

DEVICE FOR ENDOSCOPIC DELIVERY OF SURGICAL MATERIAL

Figure 1A:
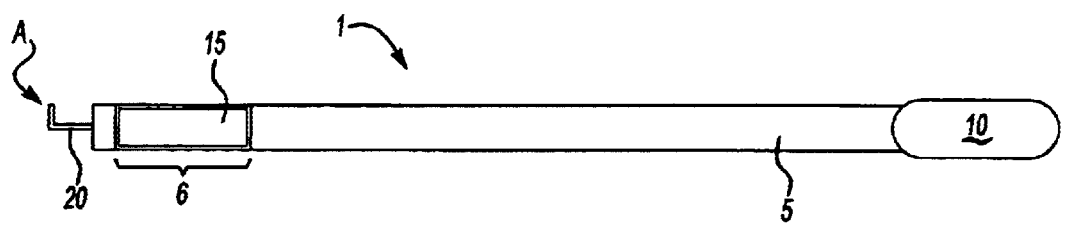

This invention relates to a delivery device.

Minimal access surgery (MAS) allows certain operations to be carried out through small access holes thus avoiding the creation of large traumatic wounds. However difficulties arise in suturing surgical incisions and ligating inside the patient using current instruments due to the small size of the access hole which restricts movement of the instrument. Tying knots in suture and ligating threads is particularly difficult and time consuming.

In an attempt to overcome this problem, devices have evolved for manipulating needles within the body. One such device (disclosed in WO92/05828) comprises a cannula which may be inserted into the body through a narrow opening. The cannula houses a piston which is slidable within the cannula and manipulates a needle. The needle is retained inside the cannula during insertion of the cannula into the patient. The needle is formed from elastic material and when retained inside the cannula, the needle is held in a generally straightened configuration. When the cannula is in place, the needle can then be projected from the end of the cannula to penetrate tissues and join wounds. Other items such as ring clips can be manipulated using the device. Several needles cane stored in the device in a straightened configuration. In such a configuration the needle s exert a force on the device in an attempt to reform to their unstressed configuration. This causes difficulty in moving the needles within the device.

According to the present invention there is provided a device for the delivery of a shape memory securing member in minimal access surgery, the device having an exit for the securing member and means to move the securing member through the exit, the device further including a magazine having a plurality of channels each of which can store a securing member.

Preferably, each securing member is restrained in the device in a first configuration, and upon passing through the exit adopts a second configuration. Also preferably, each channel is separately alignable with the exit.

One preferred form of magazine is a barrel. The barrel may be rotatable around an axis and the channels may be disposed parallel to said axis or may lie in a helical configuration. This arrangement can be likened to a "revolver barrel" on a firearm.

The first configuration in which the securing members are held inside the device is optionally straight. However, the securing members may be held in the device in a generally helical configuration. This partially relaxes the securing members and allows the use of high curvature securing members which cannot easily adopt a straightened configuration. The high curvature securing members can form tighter coils when they pass through the exit of the device.

Preferably, the second configuration is the form of a coil or loop. The coils may be overlapping (like a key ring) or may be partially open. The second configuration is preferentially adopted by the securing member in the absence of any other force. The loops of the second configuration may be round or some other shape such as a rounded oblong or a round cornered triangle. On leaving the device the securing member automatically adopts the second configuration, which is the preferred shape according to the shape memory of the member.

The channels may include or be in the form of tubes which may themselves move within the device. The securing members may be housed within the tubes. The means to move the securing members may act upon the securing members direct or upon the tubes, to move a tube and a securing member housed therein towards the exit.

When the securing members are stored within tubes, the tubes can be manipulated within the device more easily than the securing members alone. The tubes may be stored in parallel in the barrel, or may be stored sequentially in a line. The exit of the device may be so arranged as to contain the tubes but allow the securing members to pass from the tubes through the exit.

The magazine may have indexing means to align a securing member with the exit or with a second channel communicating with the exit. The indexing means may also align the securing member with the means for moving the securing member.

The magazine may also comprise other means of storing the securing members, such that the securing members are sequentially arranged in a column, line, row or helix, and are sequentially moved to the exit.

The magazine may be a replaceable element and may contain only sutures or ligatures or a selection of both, optionally in a defined order. The magazine(s) may be colour-coded for ease of use.

The means for moving the securing members may be disposed between the exit and the securing members, such that the securing members are pulled towards the exit, or alternatively, the securing members may be disposed between the exit and the means for moving the securing members, such that they are pushed towards the exit. In the first arrangement, the means for moving the securing members may comprise an inch worm motor or pinch wheel.

The exit of the device preferably comprises a tube which is curved in more than one plane optionally, the tube is curved once or twice to lie in two or three planes respectively and the exit is located at the end of the tube. The tube may be of circular cross-section or may be of a different cross-section, such as rectangular or oval.

The exit tube may be sharpened so that it can penetrate tissue before the movement of the securing members through the exit. This may be desirable where the securing members do not easily penetrate the tissue surface. Where tissue penetration by an exit tube is undesirable, the exit tube may be replaced by a tube with a wide or bulbous end. The tube may be part of a detachable assembly that allows re-orientation or extension of the assembly. The assembly can be interchangeable with other forms of assembly to allow the use of e.g., left and right hand forms and straight forms.

In an alternative form of the instrument, the exit may be embedded in a more substantial member such as a half-round continuation of the main intrument body. One or more clamping jaws acting in opposition to the exit (or its more substantial containment structure) may be incorporated in order that it can easily be penetrated by the sutures. The device than has dual suturing and grasping functions. There may be two moving jaws, one behind the other, so that two connective folds of tissue may be grasped for suturing together. Each jaw would have a cutaway to allow passage of the suture. The jaw(s) may be activated from the handle by concentric connections on the instrument axis or in the form of external tubes.

In another embodiment of the invention, an ultrasonic transducer may be incorporated in or near the exit. This may be used to excite vibrations in the suture in order to make it penetrate tissue more readily.

In some embodiments, joints between (for example) exit tubes and other tubes in the device may be in the form of collars, where one tube end fits within an end of another tube. This allows the securing members to be moved past joints between tubes more easily. Preferably, the inner faces of all tubes used are smooth.

The securing members are preferably formed from shape memory alloy such as nickel-titanium (NiTi) alloy and may comprise elongate strips of said alloy which are coiled in the absence of any deforming force. The securing members could also be formed from stainless steel, from another biocompatible material (or coated material) or from material which is resorbable by the body.

The securing members may be in the form of sutures which have at least one sharp end or may be in the form of ligatures having blunt ends. In the case of the ligature, the surgeon holds the exit of the device next to the body part to be ligated (e,g., a blood vessel) and the ligature will wrap itself around the body part as it is expelled. Securing members in the form of sutures are formed with a sharp point at the leading end. The surgeon then places the device so that the point of the exiting sutures penetrates the tissue(s) to be sutured. The suture then re-coils upon exit and creates a join in the tissue(s). Also in the case of a suture, the exit tube may be required to deliver the suture in a plane normal to the axis of the instrument.

A further advantage of the delivery device according to one embodiment of the present invention is that it can store several sutures or ligatures to allow multiple placements without the need to withdraw the instrument from the patient.

According to a second aspect of the present invention there is provided a device for the delivery of a shape memory securing member in minimal access surgery, the device having an exit for the securing member, means to move the securing member through the exit, and means for cutting the securing member, preferably once a portion thereof has been passed through the exit.

Preferably, upon leaving the device, the expelled portion of the securing member automatically adopts a configuration in accordance with its shape memory.

The device according to the second aspect of the invention preferably contains a securing member in a continuous form, such as a roll, helix or coil. The configuration of the securing member preferably changes as it passes between the interior and exterior of the device. Thus when the securing member is in the form of a high-curvature coil of shape memory alloy, it can be maintained in a relaxed state (at or near its preferred shape according to its memory) when stored within the device, and need only be subjected to stress when its configuration changes upon leaving the device.

The means for cutting the securing member is preferably disposed adjacent the exit so as to cut the securing member as it leaves the device. The means for cutting and the means for expelling may be provided by a single element, for example, a pinch wheel. The means for cutting may include means for sharpening the end of the securing member left inside the device.

The present invention further provides a shape memory securing member for use in a device as defined above, the securing member having the form of a loop, coil or a helix in the absence of any force acting upon it.

Figure 1B:
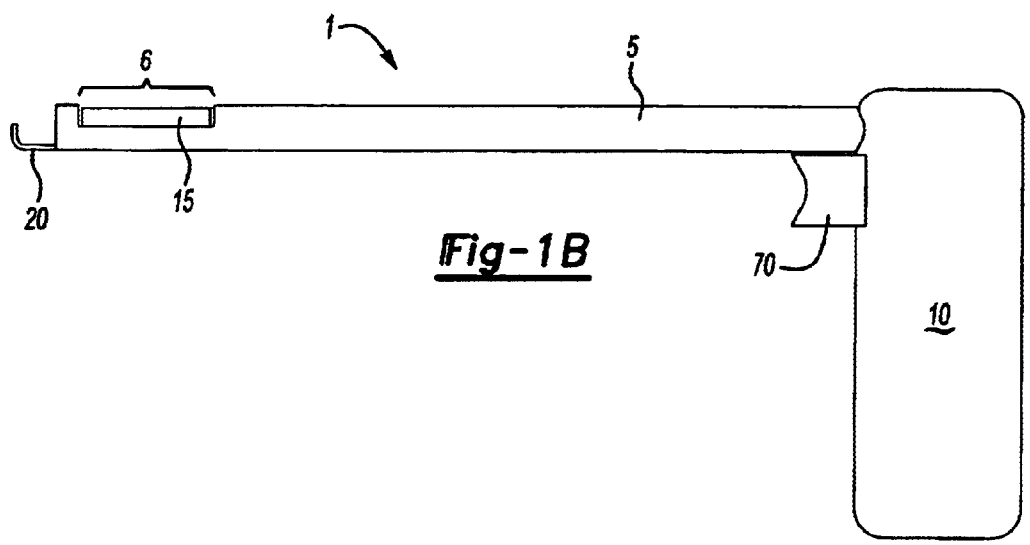
Figure 1C:
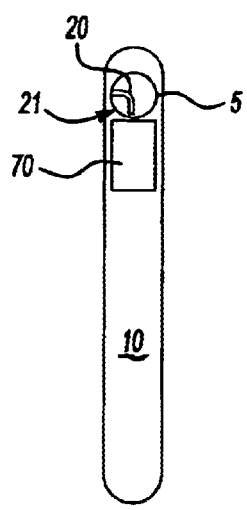
Figure 2A:
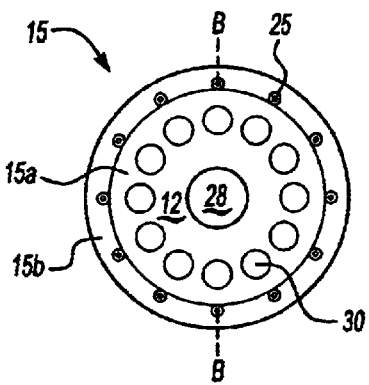
Figure 2C:
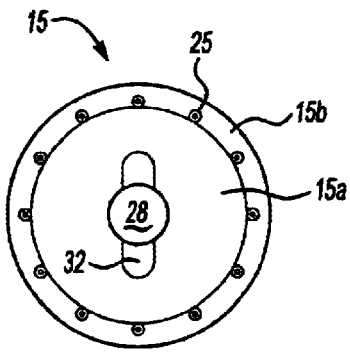
Figure 2B:
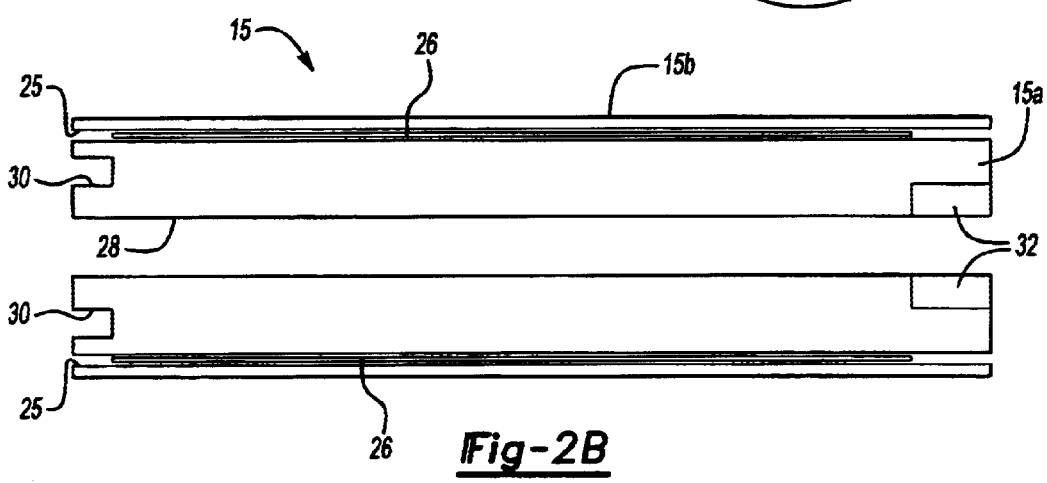
Figure 2D:
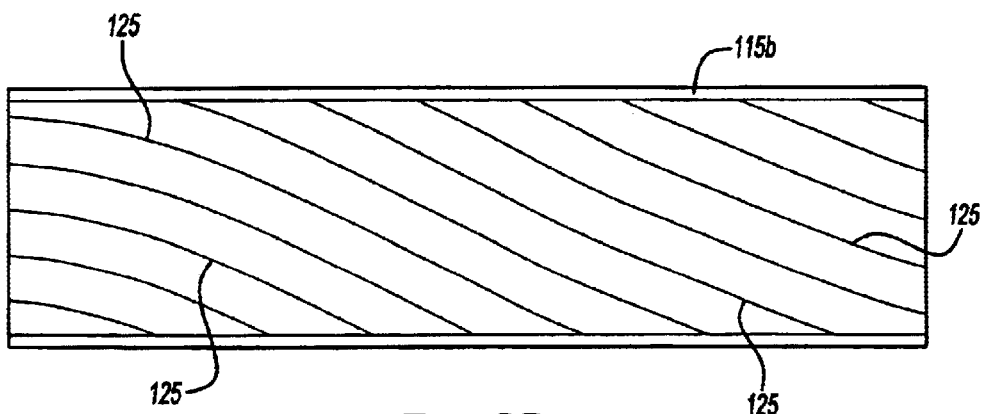
Figure 3:
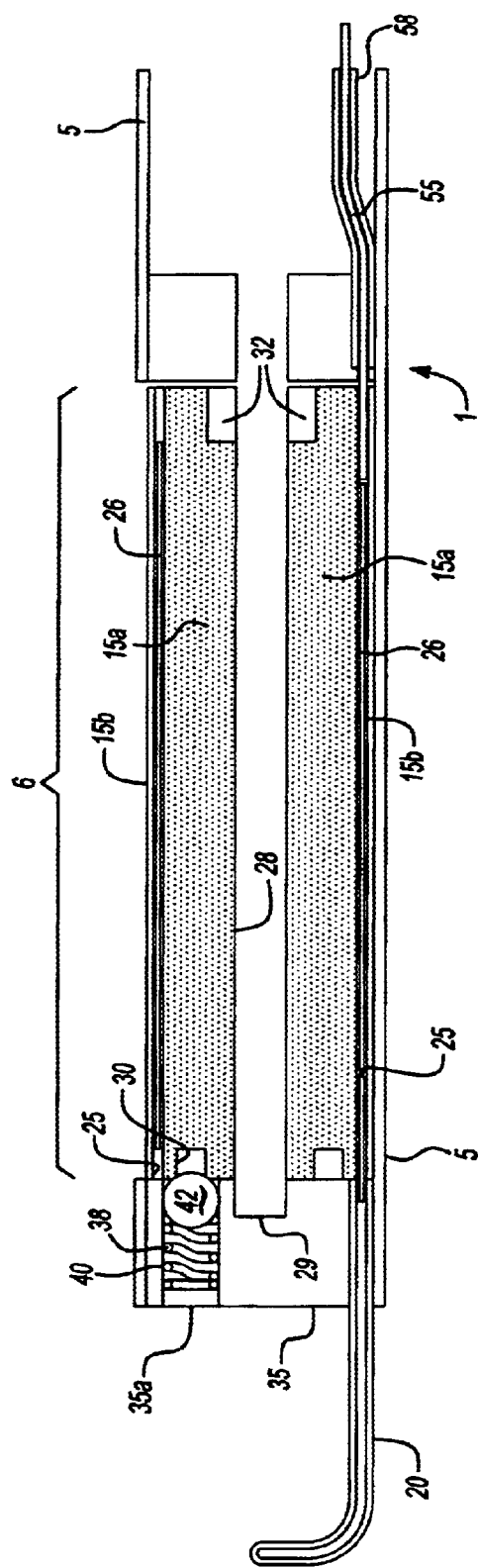
Figure 4A:
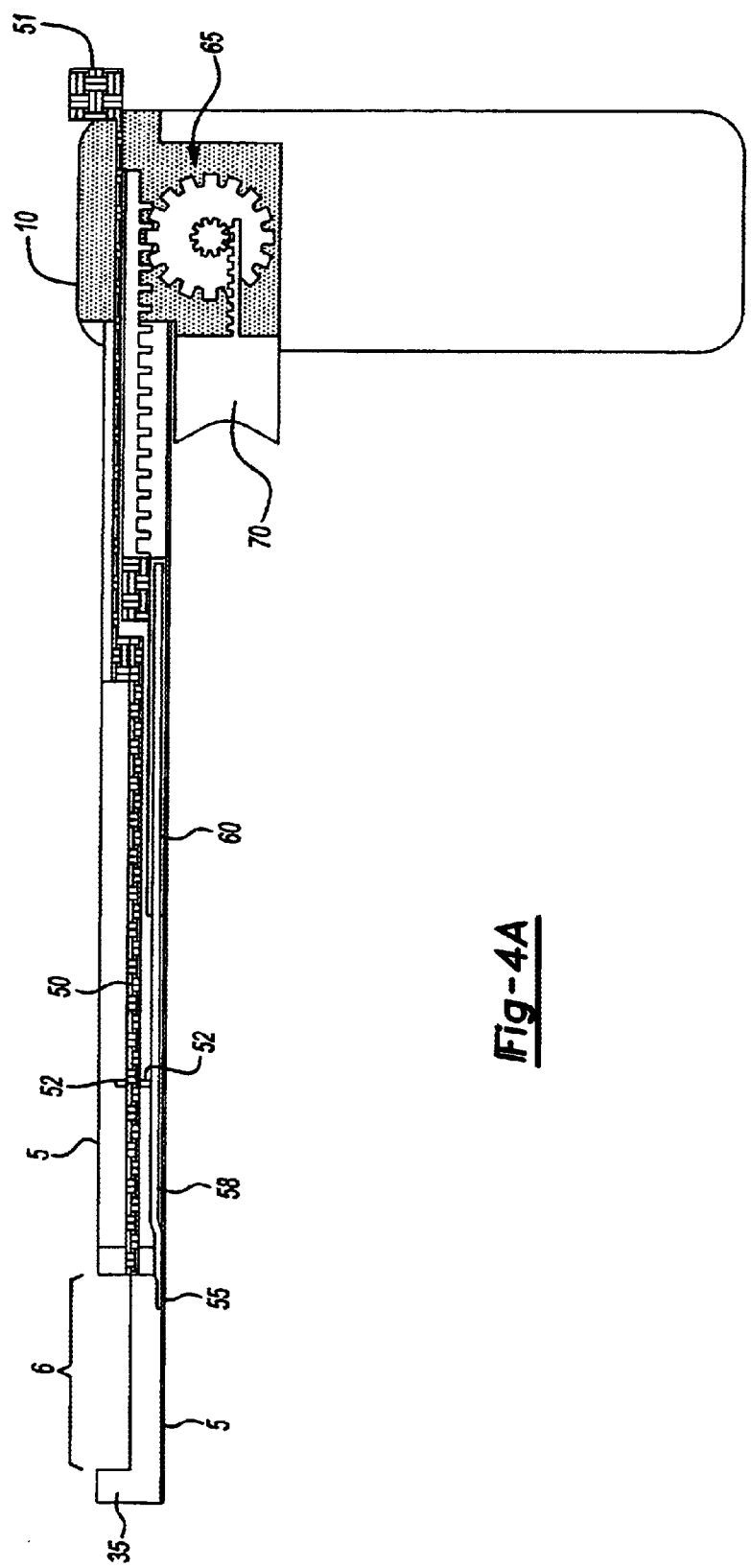

Embodiments of the present invention will now be described by way of example only and with reference to the accompanying drawings in which:

FIG. 1a shows a top view of a delivery device;
FIG. 1b shows a side view of the device of FIG. 1a;
FIG. 1c shows an end view on A of FIG. 1a.
FIG. 2a shows an end view of a barrel of the device of FIG. 1;
FIG. 2b shows a longitudinal sectional view along line B—B through the barrel of FIG. 2a;
FIG. 2c shows the opposite end view of the barrel of FIG. 2a;
FIG. 2d shows a longitudinal sectional view through a cylinder of an alternative delivery device;
FIG. 3 shows a detailed sectional view of the end of the device of FIG. 1 with the barrel of FIG. 2a in place;
FIG. 4a shows a side view of the device of FIG. 1 with the barrel of FIG. 2a removed;
FIGS. 4b and 4c show one end of second and third devices with an embedded exit and with a jaw for holding tissue against the exit; and
FIGS. 4d and 4e are schematic illustrations of parts of further alternative delivery devices.

Referring to FIGS. 1a, b and c, a delivery device 1 has a housing 5 in the form of an elongate tube of an exemplary diameter of 10 mm which has at one end a pistol grip 10 and at the other end a cut away section 6. The cut-away section 6 is adapted to accept a magazine in the form of a barrel 15 which generally conforms to the outer shape of the housing 5 so as to fit into the cut-away section 6.

The housing 5 has a exit tube 20 attached to one end thereof and communicating with the interior of the housing 5.

The exit tube 20 curves twice and has an exit 21 which faces one side of the device 1. The embodiment shown is one adapted for delivery of sutures and delivers the suture in a plane normal to the axis of the device. The device of the invention may also be used for delivering ligatures and in such a case, the exit tube preferably curves once only and the second curve shown in the exit tube 20 is not required.

Referring now to FIGS. 2a, b and c, the barrel 15 comprises an inner hollow cylinder 15a and an outer hollow cylinder 15b. The outer cylinder 15b has twelve grooves 25 on the inner surface thereof which extend along the length of the cylinder 15b. The grooves 25 are preferably formed by wire erosion and in the example shown have a diameter of 0.3 mm. The two cylinders 15a and 15b can be fitted together as shown in the drawings such that the grooves 25 form channels from one end of the barrel 15 to the other. Securing members 26 are disposed in the grooves 25 in use of the device. The securing members 26 are typically formed from shape memory alloy wire such as NiTi wire and in the present example, are 0.25 mm in diameter. The inner cylinder 15a has an axial bore 28 extending therethrough and in one end face 12 has indentations 30 which extend a short distance into the cylinder 15a in an axial direction. In the opposite end face of the inner cylinder 15a is a slot 32 which intersects with the end of the bore 28.

FIG. 2d shows a longitudinal sectional view of an outer hollow cylinder 115b of an alterative delivery device. The outer cylinder 115b includes grooves 125 in a helical configuration.

Referring now to FIG. 3, the end of the device 1 which holds the barrel 15 has an end stop 35 located after the cut-away section 6. The end stop has an axial indentation or bore 29 on the internal face extending at least partially along the axis of the end stop 35 and which is co-axial with bore 28 when the barrel 15 is in place in the cut-away section 6. The end stop 35 also has an annular arrangement of twelve bores 38 in its inner face in which are located springs 40 and ball bearings 42. The springs 40 bear on portions 35a of the outer wall of end stop 35 and exert force on the ball bearing 42 so as to expel them from the bores 38 in the direction of the pistol grip 10. Typically, the ball bearings 42 are restrained from leaving the bores 38 entirely and may be held captive on the springs 38 or embedded in the end stop 35.

When the barrel 15 is in place in the cut-away section 6, the ball bearings 42 are forced out of the bores 38 and engage with the indentations 30 in the barrel 15. Thus a series of twelve detent positions is established.

An axle 50 (shown in FIG. 4a) is withdrawn from the cut-away section 6 by a handle 51. The barrel 15 (not shown in FIG. 4a) is loaded with twelve securing members such as sutures 26 formed from NiTi shape memory alloy, and is located in the cut-away section 6. The sutures 26 are held in a generally straightened configuration in the grooves 25 of the barrel 15. The axle 50 is then moved towards the end stop 35 by manipulating the handle 51 such that the axle 50 passes through the bore 28 and engages in the axial bore 29 in the end stop 35. Additionally a pair of projections 52 on the axle 50 are disposed in the slot 32 on the barrel 15 thereby locking the barrel 15 against axial rotation with respect to the axle 50. The barrel 15 is thereby locked in place in the cut-away section 6 and can be rotated through its detent positions by manipulation of the axle 50. The detent positions are held by the action of the ball bearings 42 engaging in the indentations 30.

The barrel 15 is released by sliding back the handle 51 so as to disengage the projections 52 from the slots 32 and the axle 50 from the bore 28. The barrel 15 can then be removed and reloaded or replaced with one already loaded.

In each of the detent positions a respective one of the grooves 25 is in line with the exit tube 20, thus allowing a securing member such as a suture or ligature 26 to be expelled from the groove 25 through the exit tube 20 and out of the exit 21.

The housing 5 also includes a flexible push wire 55 which is supported in a guide tube 58. The end of the guide tube 58 is in line with the exit tube 20 and with a respective one of the grooves 25 when the barrel 15 is in a detent position.

The push wire 55 is slidable in the guide tube and can be moved so as to protrude into a respective one of the grooves 25 when the barrel 15 is in a detent position in the cut-away section 6. The push wire 55 is clamped by a sliding clamp 60 which is moved by a rack and pinion mechanism 65 located in the pistol grip 10. The rack and pinion mechanism 65 is in turn activated by a trigger 70.

The rack and pinion mechanism 65 has gears which increase the movement of the trigger 70 and reverse its direction so as to advance the clamp 60 towards the barrel 15 located in the cut-away section 6.

Movement of the push wire 55 along the support tube 58 and into the groove 25 expels a securing member 26 located therein from the exit tube 20. Thus actuation of the trigger 70 causes the push wire 55 to push a securing member 26 from one of the grooves 25 out of the exit tube 20. Upon leaving the exit tube 20, the securing member 26 no longer has any force acting upon it to maintain it in its straightened configuration, and it re-coils into its preferred shape memory configuration of a loop or coil.

The movement of the trigger 70 could also cause the barrel 5 to rotate through one detent position so that the next groove 25 is aligned with the exit tube 20 and the support tube 58. The barrel-rotation mechanism (not shown) is similar to the mechanisms found in some ball-point pens.

Different barrels may hold different securing members for different purposes, or a single barrel may hold a number of different securing members.

FIG. 4b shows the end of a second device according to the present invention, having its exit 72 embedded in a semi-circular extension 74 of the main body of the device 76. Adjacent the exit 72 is a moveable clamping jaw 78, in which is a cutaway 80 through which an exiting securing member can pass. Tissue can be grasped between the exit 72 and the jaw 78. FIG. 4c shows a third device having two moveable jaws 82 opposite the device exit 84.

FIG. 4d shows a schematic illustration of an alternative delivery device 101, similar to the device 1 of FIGS. 1 to 4a but including an ultrasonic transducer 86 near an exit tube 120, used to excite vibrations in the sutures.

FIG. 4e shows a schematic illustration of a further alternative delivery device 201, similar to the device 1 of FIGS.1 to 4a, but including means 88 for moving the securing members disposed between an exit tube 220 and the securing members. The means 88 may also form means for cutting the securing member and may comprise, for example, a pinch wheel.

Modifications and improvements may be incorporated without departing from the scope of the invention.

What is claimed is:

1. A device for the delivery of a shape memory securing member in minimal access surgery, the device having an exit for the securing member and means to move the securing member through the exit, the device further including a magazine having a plurality of channels which include or are in the form of tubes, each of which can store a securing member and at least one shape memory securing member.

2. A device as claimed in claim 1 wherein each channel of the magazine is separately alignable with the exit.

3. A device as claimed in claim 1 wherein the or each securing member is restrained in the device in a first configuration, and upon passing through the exit adopts a second configuration.

4. A device as claimed in claim 1 wherein the or each securing member is made from nickel-titanium alloy or stainless steel.

5. A device as claimed in claim 1 wherein the magazine is a barrel.

6. A device as claimed in claim 5 wherein the barrel is rotatable about an axis.

7. A device as claimed in claim 6 wherein the channels are arranged along the barrel and disposition parallel with the axis.

8. A device as claimed in claim 1 wherein the magazine is lockable within the device.

9. A device as claimed in claim 1 wherein the magazine is loaded with a plurality of securing members.

10. A device as claimed in claim 1 wherein the magazine has indexing means to align a securing member with the exit or with a second channel communicating with the exit.

11. A device as claimed in claim 10 wherein the indexing means aligns the securing member with the means for moving the securing member.

12. A device as claimed in claim 1 wherein the magazine is removable from the device.

13. A device as claimed in claim 1 wherein the or each securing member is disposed between the exit and the means for moving the securing member.

14. A device as claimed in claim 1 wherein the exit comprises an exit tube.

15. A device as claimed in claim 14 wherein the exit tube is detachable.

16. A device as claimed in claim 1 wherein the device includes one or more clamping jaws for grasping tissue, said one or more clamping jaws disposed adjacent the exit.

17. A device as claimed in claim 16 wherein one or more of the jaws is moveable, and wherein a securing member is passable through one or more of the jaws.

18. A device as claimed in claim 1 for use as a surgical instrument.

19. A device as claimed in claim 18 wherein the securing member is a suture or a ligature.

20. A device as claimed in claim 1 wherein the device includes a handle and includes a trigger means to operate the means to move the securing member.

21. A method of delivering a securing member in minimal access surgery using a device as defined in claim 1 wherein at least the exit of the device is located within the confined space, and the means to move the securing member is activated to deliver the securing member from the device through the exit.

22. A method as claimed in claim 21 wherein the securing member changes from a first configuration in the device to a second configuration upon passing through the exit.

23. A device for the delivery of a shape memory securing member in minimal access surgery, the device having an exit for the securing member, means to move the securing member through the exit, means for cutting the securing member or a portion of the securing member that has passed through the exit and a shape memory securing member.

24. A device as claimed in claim 23 wherein the expelled portion of the securing member automatically adopts a configuration in accordance with its shape memory.

25. A device as claimed in claim 24 wherein the adopted configuration is a coil or loop.

26. A device as claimed in claim 23 wherein the securing member in the device is in a continuous form.

27. A device as claimed in claim 26 wherein the configuration of the securing member changes as it passes between the interior and exterior of the device.

28. A device as claimed in claim 23 wherein the means for cutting the securing member is disposed adjacent to the exit.

29. A device for the delivery of a shape memory securing member in minimal access surgery, the device having an exit for the securing member and means to move the securing member through the exit, the device further including a magazine having a plurality of channels which include or are in the form of tubes, each of which can store a securing member.

30. A device for the delivery of a shape memory securing member in minimal access surgery, the device having an exit for the securing member and means to move the securing member through the exit, the device further including a magazine having a plurality of channels each of which can store a securing member and an ultrasonic transducer located in or near the exit.

31. A device for the delivery of a shape memory securing member in minimal access surgery, the device having an exit for the securing member, means to move the securing member through the exit, and at least one shape memory securing member, the device further including a magazine in the form of a barrel which is rotatable about an axis and having a plurality of channels arranged along the barrel and disposed in a helical configuration with respect to the axis, wherein each channel can store a securing member.

32. A device for the delivery of a shape memory securing member in minimal access surgery, the device having an exit for the securing member and means to move the securing member through the exit, the device further including a magazine having a plurality of channels each of which can store a securing member and at least one shape memory securing member, wherein the or each securing member is restrained in the device in a first configuration, and upon passing through the exit adopts a second configuration which is in the form of a coil or loop.

33. A device for the delivery of a shape memory securing member in minimal access surgery, the device having an exit for the securing member and means to move the securing member through the exit, the device further including a magazine having a plurality of channels each of which can store a securing member and at least one shape memory securing member, and wherein the or each securing member is restrained in the device in a first configuration, and upon passing through the exit adopts a second configuration which is the preferred shape according to the shape memory of the securing member.

34. A device for the delivery of a shape memory securing member in minimal access surgery, the device having an exit for the securing member and means to move the securing member through the exit, the device further including a magazine having a plurality of channels each of which can store a securing member and at least one shape memory securing member, and wherein the means for moving the securing is disposed between the exit and the or each securing.

35. A device for the delivery of a shape memory securing member in minimal access surgery, the device having an exit for the securing member and a push wire to move the securing member through the exit, the device further including a magazine having a plurality of channels each of which can store a securing member and at least one shape memory securing member, and wherein the or each securing member is disposed between the exit and the push wire.

36. A device as claimed in claim 35 wherein the push wire is flexible and slidable in a guide tube.

37. A device for the delivery of a shape memory securing member in minimal access surgery, the device having a sharpened exit tube for the securing member and means to move the securing member through the sharpened exit tube, the device further including a magazine having a plurality of channels each of which can store a securing member and at least one shape memory securing member.

38. A device for the delivery of a shape memory securing member in minimal access surgery, the device having a curved exit tube for the securing member and; means to move the securing member through the curved exit tube, the device further including a magazine having a plurality of channels each of which can store a securing member and at least one shape memory securing member.

39. A device for the delivery of a shape memory securing member in minimal access surgery, the device having an exit for the securing member and means to move the securing member through the exit, the device further including a magazine having plurality of channels each of which can store a securing member, at least one shape memory securing member and an ultrasonic transducer located in or near the exit.

* * * * *

UNITED STATES PATENT AND TRADEMARK OFFICE
CERTIFICATE OF CORRECTION

PATENT NO.     : 6,699,255 B1
DATED          : March 2, 2004
INVENTOR(S)    : Alfred Cushchieri and Grahm Timothy Frank Page 1 of 1

It is certified that error appears in the above-identified patent and that said Letters Patent is hereby corrected as shown below:

<u>Column 8,</u>
Line 25, please insert -- member -- after the word "securing."
Line 26, please insert -- member -- after the word "securing."
Line 46, please delete ";" after the word "and."
Line 55, please insert -- a -- after the word "having."

Signed and Sealed this

Fifteenth Day of June, 2004

JON W. DUDAS
*Acting Director of the United States Patent and Trademark Office*